(12) United States Patent
Shabino

(10) Patent No.: US 7,049,824 B2
(45) Date of Patent: May 23, 2006

(54) DIFFERENTIAL PARTICULATE DETECTION SYSTEM FOR ELECTRONIC DEVICES

(75) Inventor: Peter James Shabino, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 158 days.

(21) Appl. No.: 10/401,316

(22) Filed: Mar. 27, 2003

(65) Prior Publication Data

US 2004/0189313 A1    Sep. 30, 2004

(51) Int. Cl.
  *G01N 27/62* (2006.01)
  *G08B 17/10* (2006.01)

(52) U.S. Cl. .................. 324/464; 340/629; 340/630

(58) Field of Classification Search ............. 324/459, 324/464, 71.4, 207.13, 207.22; 73/627, 628, 73/61.71, 861.41, 861.73, 863.31, 865.5; 340/627–630, 529, 693.6; 454/141, 142, 454/145, 171, 234, 241; 169/56, 60, 61
See application file for complete search history.

(56) References Cited

U.S. PATENT DOCUMENTS

| | | | | |
|---|---|---|---|---|
| 3,953,844 A * | 4/1976 | Barr et al. | ................ | 340/627 |
| 4,035,788 A * | 7/1977 | Barr | ................ | 340/627 |
| 4,208,655 A * | 6/1980 | Phillips | ................ | 340/627 |
| 4,223,559 A * | 9/1980 | Chuan et al. | ................ | 73/865.5 |
| 4,254,414 A * | 3/1981 | Street et al. | ................ | 340/627 |
| 4,335,378 A * | 6/1982 | Coleman | ................ | 340/629 |
| 4,544,273 A * | 10/1985 | Berndt | ................ | 356/434 |
| 4,637,473 A * | 1/1987 | Gillis et al. | ................ | 169/61 |
| 4,764,758 A * | 8/1988 | Skala | ................ | 340/627 |
| 5,001,463 A * | 3/1991 | Hamburger | ................ | 340/627 |
| 5,356,334 A * | 10/1994 | Gray | ................ | 454/51 |
| 5,428,964 A * | 7/1995 | Lobdell | ................ | 62/176.6 |
| 5,519,382 A * | 5/1996 | Pope et al. | ................ | 340/627 |
| 5,554,416 A * | 9/1996 | Scheufler et al. | ................ | 427/378 |
| 5,691,703 A * | 11/1997 | Roby et al. | ................ | 340/627 |
| 5,917,417 A * | 6/1999 | Girling et al. | ................ | 340/628 |
| 6,117,190 A * | 9/2000 | Chao et al. | ................ | 8/137 |
| 6,125,710 A * | 10/2000 | Sharp | ................ | 73/863.31 |
| 6,394,062 B1 * | 5/2002 | Daly et al. | ................ | 123/198 E |
| 6,708,487 B1 * | 3/2004 | Morimoto et al. | ................ | 60/311 |
| 6,876,305 B1 * | 4/2005 | Kadwell et al. | ................ | 340/630 |
| 2003/0051023 A1 * | 3/2003 | Reichel et al. | ................ | 709/223 |

* cited by examiner

*Primary Examiner*—Vincent Q. Nguyen
*Assistant Examiner*—Hoai-An D. Nguyen
(74) *Attorney, Agent, or Firm*—James R. Nock

(57) ABSTRACT

A method, apparatus and program product for differential particle detection in electronic devices is provided. A first particulate sensor is positioned in proximity to an air intake of the electronic device. A second particulate sensor is positioned in proximity to the air exhaust of the device. A comparator compares the particulate concentrations detected by the first and second particulate sensors. Differential particle detection between the air intake and air exhaust of an electronic device enables early detection of potential fire conditions existing within the electronic device.

19 Claims, 4 Drawing Sheets

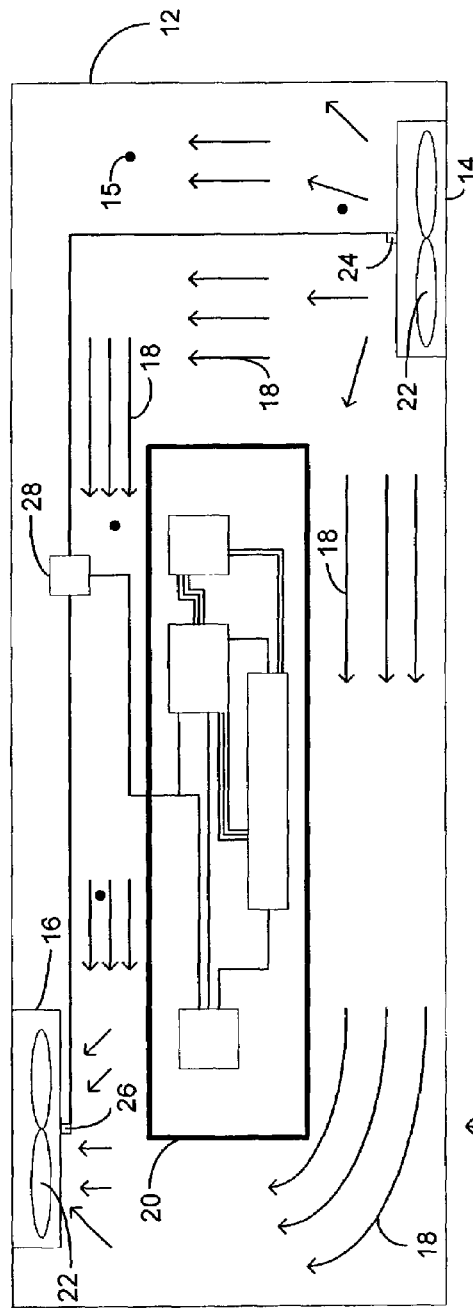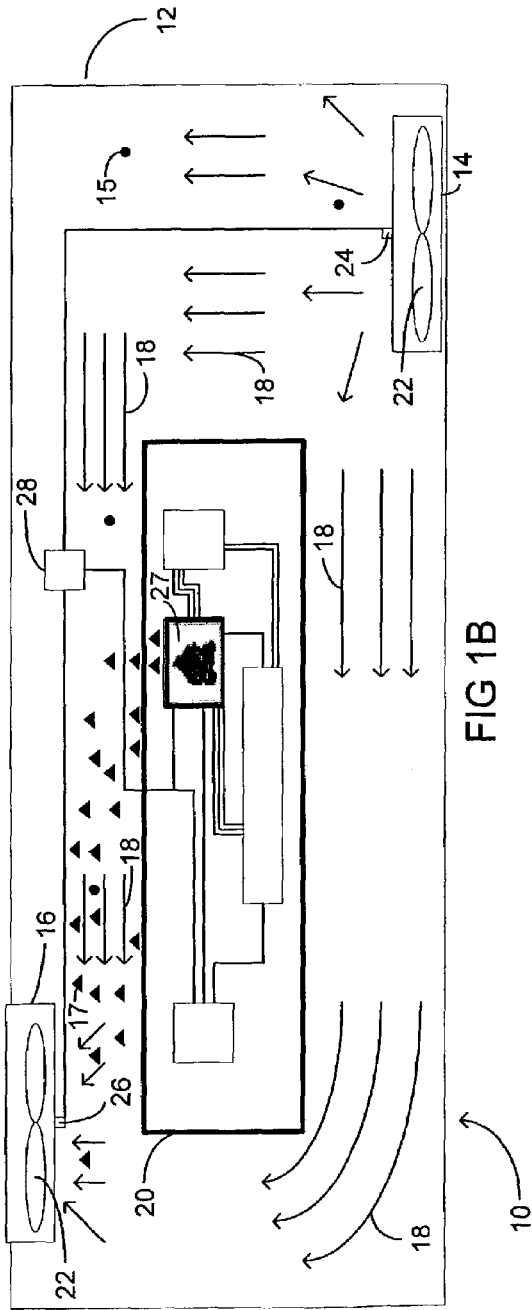

DIFFERENTIAL PARTICULATE DETECTION SYSTEM FOR ELECTRONIC DEVICES

FIELD OF THE INVENTION

The present invention relates generally to the detection of particulates in electronic devices, and more specifically to the differential detection of particulate matter between the air intake and air exhaust of an electronic device.

BACKGROUND OF THE INVENTION

Accidental fires due to electrical causes can come from nearly every electrical device in the home or business. Some electrical fires take a long time to develop, some happen in an instant. As one example, power supply component malfunctions can occasionally occur in all electronic devices such as consumer electronics, audio/video equipment, and personal computers and monitors.

Even sophisticated electronic devices such as large computer systems can be susceptible to heat-generating defects, such as power-to-ground shorts. In such computer systems, the difference between a normally functioning system and a shorted system can be in the milli-Ohms. Thus, if power supply operational tolerances for a computer system are set too conservatively, the system runs the risk of false shutdowns, even when the system is operating normally. Likewise, if power supply operational tolerances are set too aggressively, the system runs the risk of possible system damage and/or fires due to shorts.

Several approaches have been taken to enhance the early detection of conditions which can lead to shorts/fires in electronic devices. U.S. patent application Ser. No. 10/268,738, filed Oct. 10, 2002, entitled, "Conformal Coating Enhanced to Provide Heat Detection" outlines one such approach. In this application, a coating is provided which will emit a particular gas when heated to a particular temperature. This coating is applied to an object to which pre-damage heat detection is desired (e.g., a circuit board/electronic component in an electrical device). One or more sensors are then installed in proximity to the coated components such that when a component reaches a particular operating temperature, the coating begins to emit a gas which is detected by the sensor. In this way, damage can be prevented to components from excess heat, and subsequent electrical fires can be prevented.

There is a need for a simple, low-cost alternative to fire detection within electronic devices. Such an alternative should utilize simple, off-the-shelf electronic components to provide the detection. Such detection should be usable in a wide variety of environmental conditions.

SUMMARY OF THE INVENTION

The present invention provides an apparatus for differentially detecting the concentration of particulates at an air intake and air exhaust of an electronic device. The apparatus includes a first particulate sensor positioned in proximity to the air intake, and a second particulate sensor positioned in proximity to the air exhaust. The apparatus further includes a comparator for comparing a first particulate concentration from the first particulate sensor against a second particulate concentration from the second particulate sensor.

In one embodiment of the present invention, the first and second particulate sensors are photo optic type particle detectors. In an alternate embodiment, the first and second particulate sensors are ionization type particle detectors.

In one embodiment of the present invention, if the comparator determines that the difference between the first particulate concentration and the second particulate concentration exceeds a predetermined threshold, an alert signal is raised by the comparator. This alert signal can cause the electronic device to shut down. The alert signal may also cause the electronic device to issue a warning to the user of the device.

In another embodiment of the present invention, if the comparator determines that the difference between the first particulate concentration and the second particulate concentration exceeds a predetermined threshold for at least a predetermined period of time, an alert signal is raised by the comparator. In one embodiment, this alert signal causes the electronic device to shut down. The alert signal may also cause the electronic device to issue a warning to the user of the device.

The present invention also provides a method of detecting a potential fire within an electronic device. The method begins by detecting a first particulate concentration at a first particulate sensor positioned in proximity to an air intake of the electronic device.

Next, the method detects a second particulate concentration at a second particulate sensor positioned in proximity to an air exhaust of the electronic device. Next, the method compares the first particulate concentration from the first particulate sensor against the second particulate concentration from the second particulate sensor.

In one embodiment of the present invention, the method further includes the step of issuing a warning to a user of the electronic device if the second particulate concentration exceeds the first particulate concentration by a predetermined margin. Also, the method may also include a step of issuing a warning to a user of the electronic device if the second particulate concentration exceeds the first particulate concentration by a predetermined margin for a predetermined time interval.

In another embodiment of the present invention, the method includes the step of shutting down the electronic device is the second particulate concentration exceeds the first particulate concentration at a given time by a predetermined margin.

The present invention further provides a program product having signal bearing media, and a fire detection routine stored on the signal bearing media. The fire detection routine performs the steps of detecting a first particulate concentration at a first particulate sensor positioned in proximity to an air intake of the electronic device; detecting a second particulate concentration at a second particulate sensor positioned in proximity to an air exhaust of the electronic device; and comparing the first particulate concentration from the first particulate sensor against the second particulate concentration from the second particulate sensor.

BRIEF DESCRIPTION OF THE DRAWINGS

FIG. 1A illustrates an enclosure for an electrical device, within which one embodiment of the present invention is deployed, wherein the electrical device is operating normally.

FIG. 1B illustrates an enclosure for an electrical device, within which one embodiment of the present invention is deployed, wherein a fire is burning within the electrical device.

DETAILED DESCRIPTION OF THE PREFERRED EMBODIMENTS

Figure 2A:
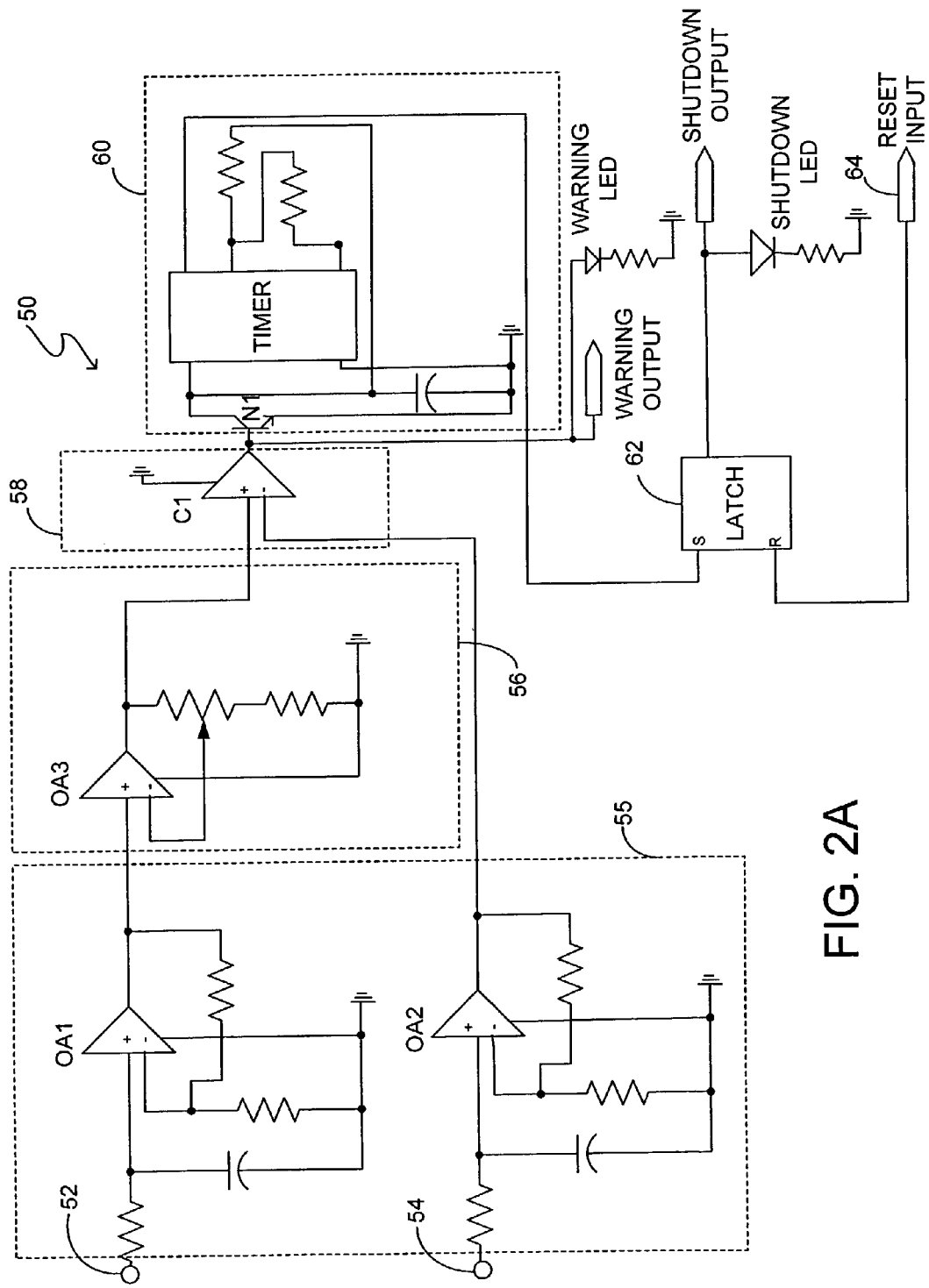
FIG. 2A illustrates a circuit diagram of a preferred embodiment of the present invention.
Figure 2B:
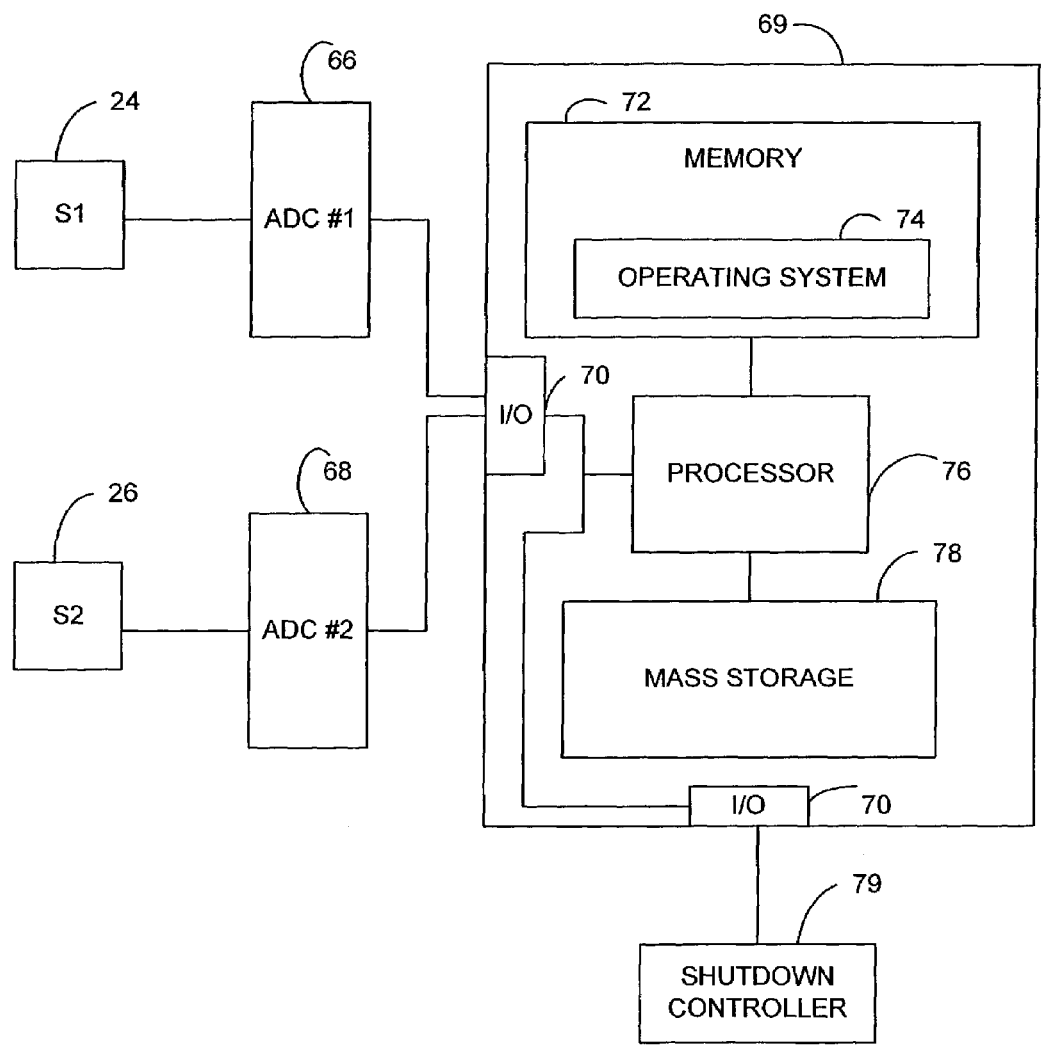
FIG. 2B illustrates a computer system, wherein the present invention resides on signal bearing media within the computer system.
Figure 3:
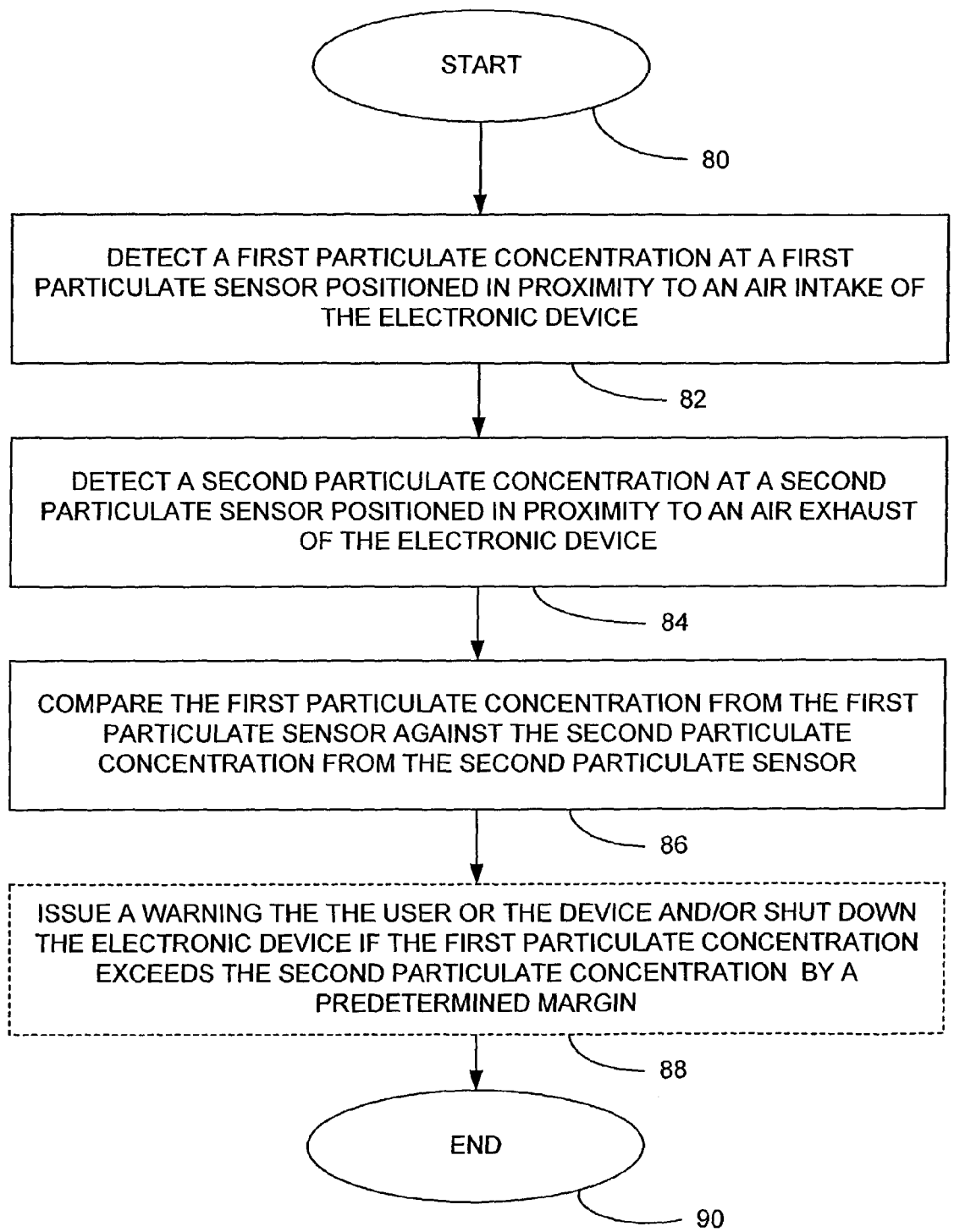
FIG. 3 is a block diagram of a method of detecting a potential fire within an electronic device, in accordance with the present invention.

Turning to the Drawings, wherein like numbers denote like parts throughout the several views, FIGS. 1–3 are used to explain how the present invention can be used in the context of a computer system. However, it should be understood that the scope and teachings of the present invention are not limited to the context presented in the discussion of the preferred and alternate embodiments. Indeed, the teachings of the present invention can be applied to any sort of object for which the differential detection of particulates (e.g., fire detection) is desired, no matter whether the object is an electronic device, electromechanical device, or some other type of object for which fire detection is important.

FIG. 1A illustrates an enclosure for an electrical device (e.g., computer system) 10. Electrical device 10 includes a case 12, which further includes an air intake 14, an air exhaust 16, and an air circulation path 18. Electrical device 10 further includes a component assembly 20 which forms the heart of the electrical device. Component assembly 20 typically includes circuit boards, memories, processors, power supplies and other electronic components which provide functionality to the electrical device. In a typical embodiment, component assembly 20 is placed within air circulation path 18 such that air circulating past the component assembly removes the heat inherently generated during normal operation of the component assembly. In most instances, one or more fans 22 may be placed at air intake 14 and/or air exhaust 16 in order to maximize air circulation within the electrical device.

In the present invention, a first particulate sensor 24 is positioned in proximity to the air intake 14 of electrical device 10. A second particulate sensor 26 is positioned in proximity to the air exhaust 16 of electrical device 10. As air from the external environment is drawn into electrical device 10, first particulate sensor 24 measures the concentration of particulates 15 of the air passing into the device. This air is then circulated past the electronic components of the component assembly 20, and is then exhausted out of the device through air exhaust 16. As the air passes through air exhaust 16, second particulate sensor 26 measures the concentration of particulates 15 of the air passing out of the device to the external environment.

During normal operation of the device, the concentration of particulates 15 sensed by the first particulate sensor 24 will be roughly equivalent to the concentration of particulates 15 sensed by the second particulate sensor 26, since the circulation of the air past component assembly 20 should have no material effect on the concentration of particulates 15 within the air passing by it. However, if component assembly is smoldering or is on fire (as illustrated at element 27 of FIG. 1B), additional particulate matter 17 introduced by the smoke/fire will enter into the circulating air, and as the additional particulate matter 17 is entrained past air exhaust 16, the second particulate sensor 26 will register a significantly higher concentration of total particulate matter (i.e., particulates 15 and additional particulate matter 17) than was registered in the air at the first particulate sensor 24.

A comparator 28 compares the particulate concentration between the first particulate sensor 24 and the second particulate sensor 26. Comparator 28 is programmed to accept a predefined threshold of variance between the particulate readings at the first and second sensors, in order to reduce/eliminate false indications of an alert condition. In other words, the difference between the particulate readings at the first and second sensors 24 and 26 must exceed a predetermined threshold for an alert to be generated.

In one embodiment of the present invention, comparator 28 may also require that the difference between the particulate readings at the first and second sensors 24 and 26 exceed a predetermined threshold for a predetermined period of time in order to generate an alert. Once again, this is done to reduce/eliminate false alert conditions.

Once comparator 28 determines that the difference in particulate concentrations between the first and second sensors 24 and 26 exceeds a predetermined threshold, several actions may be taken. In a first embodiment, an alert is issued to the user of the device, through a visual or audible indicator, such as an alert light or an audible alarm. In another embodiment, if comparator 28 determines that a fire may be present, a signal is generated which causes an immediate shutdown of the electronic device. In yet another embodiment, an electronic warning is issued to a local fire department, or to a building manager. Finally, a warning signal can be issued to other devices within the network, alerting them to the condition.

In a preferred embodiment of the present invention, first and second particulate sensors, 24 and 26 respectively, are photo optic/photoelectric type sensors. These sensors are generally available from a variety of electronic suppliers, such as System Sensor, Inc. In a preferred embodiment of the present invention, first and second particulate sensors 24 and 26 have proportional outputs (output voltage goes up or down with changes in concentration of particles in the air). In alternate embodiments of the present invention, particulate sensors 24 and 26 are ionization type particulate sensors.

FIG. 2A illustrates a circuit diagram of a preferred embodiment of the present invention, shown generally at 50. Input 52 is an input from first particulate sensor 24 (i.e., the sensor positioned near the air intake of the device). Input 54 is an input from second particulate sensor 26 (i.e., the sensor positioned near the air exhaust of the device). The signals provided at inputs 50 and 52 are analog outputs from particulate sensors proportional to the concentration of particles in the air stream.

A signal conditioner 55 conditions the signal provided from inputs 52 and 54, filtering out any system noise present on the signals. Signal conditioner 55 may not be needed in all instances. A hystresis stage 56 is used to set a buffer zone between the input sensors and the output. This hystresis stage 56 serves to cut down on false triggers due to signal drift. A comparator stage 58 will bring its output active (i.e., raise an alert signal) if the particle concentration detected by the second particulate sensor 26 exceeds the particle concentration detected by first particulate sensor 24 by a predefined margin. In one embodiment, the output of comparator stage 58 is also used to drive a warning LED. Time delay stage 60 is used to verify that an actual fault is present. If the comparator stage 58 output is active, but the output does not stay active for a predetermined time period, time delay stage 60 will effectively "filter" the active output from the comparator as a false alarm. If the comparator stage 58 output remains active longer than the predetermined time period, an alert signal will be generated which is then passed to a shutdown latch 62. Shutdown latch 62 latches the alert signal which then activates the shutdown of the electrical device. Shutdown latch 62 will remain active until a reset signal is received by the shutdown latch. Reset input 64 is generated by the electrical device in order to clear the shutdown signal from the shutdown latch 62.

FIG. 2B illustrates an alternate embodiment of the present invention, wherein the analog outputs from first and second particulate sensors 24 and 26, are digitized, then passed to a computer system 69 for processing. In this embodiment, an analog signal representing a particulate concentration at first particulate sensor 24 of an electronic device is passed through a first analog-to-digital converter 66, then the resultant digital signal is passed to computer system 69 via I/O port 70. In a similar manner, the analog signal representing a particulate concentration at second particulate sensor 26 within the electronic device is passed through a second analog-to-digital converter 68, then the resultant digital signal is passed to computer system 69 via I/O port 70. Computer system 69 includes memory 72 which, in turn, includes an operating system 74. Computer system 69 further includes a processor 76 which executes a fire detection computer program to differentially compare the digital signals from analog-to-digital converters 66 and 68. This fire detection computer program then compares the results of the differential comparison from the analog-to-digital converters 66 and 68 to determine if a potential fire condition exists within the electronic device being monitored, and issues an appropriate warning and/or drives a signal to a shutdown controller 79 to shutdown the device if a fire condition is detected. The fire detection computer program resides on signal bearing media within the computer system, such as mass storage device 78. As with the analog system of FIG. 2A, warning LEDs, audible alarms, and external alerts can be programmed. Timing functions inside processor 76 can be programmed to prevent false alarms.

FIG. 3 is a block diagram of a method of detecting a potential fire within an electronic device, in accordance with the present invention. The method begins at block 80. At block 82 the method begins by detecting a first particulate concentration at a first particulate sensor positioned in proximity to an air intake of the electronic device. Next, at block 84, the method detects a second particulate concentration at a second particulate sensor positioned in proximity to an air exhaust of the electronic device. At block 86, the method next compares the first particulate concentration from the first particulate sensor 24 against the second particulate concentration from the second particulate sensor 26. At block 88, the method optionally issues a warning to the user of the device and/or shuts down the electronic device if the first particulate concentration exceeds the second particulate concentration by a predetermined margin. In an alternative embodiment (not shown), the method issues a warning to the user of the device and/or shuts down the electronic device if the first particulate concentration exceeds the second particulate concentration by a predetermined margin for at least a predetermined amount of time. This additional requirement helps to reduce the amount of false alarms generated by the apparatus. At block 90, the method ends.

While the present invention has been illustrated by a description of various embodiments and while there embodiments have been described in considerable detail, it is not the intention of the applicants to restrict or in any way limit the scope of the appended claims to such detail. For example, while the present invention has been described in the context of fire detectors for electronic devices, those skilled in the art will appreciate that the mechanisms of the present invention are capable of being distributed as a program product in a variety of forms, such as a program/routine for a computer system running a variety of operating systems, and that the present invention applies equally regardless of the particular type of signal bearing media to actually carry out the distribution. Examples of signal bearing media include: recordable type media such as floppy disks (e.g., a floppy disk) and CD ROMS, and transmission type media such as digital and analog communication links, including wireless communication links.

The invention in its broader aspects is therefore not limited to the specific details, representative apparatus and method, and illustrative examples shown and described. Accordingly, departures may be made from such details without departing from the spirit or scope of applicants' general inventive concept. It is intended that the scope of the present invention be limited not by this detailed description, but rather by the claims appended hereto. Therefore, the invention lies in the claims hereinafter appended.

What is claimed is:

1. An apparatus for differentially detecting a particulate concentration at an air intake and an air exhaust of an electronic device, the apparatus comprising:
    a first particulate sensor positioned to measure a first particulate concentration of all air passing into the electronic device;
    a second particulate sensor positioned to measure a second particulate concentration of all air passing out of the electronic device;
    a comparator for comparing the first particulate concentration against the second particulate concentration, in order to detect an incipient fire condition within the electronic device.

2. The apparatus of claim 1, wherein the first particulate sensor and the second particulate sensor are photo optic type particle detectors.

3. The apparatus of claim 1, wherein the first particulate sensor and the second particulate sensor are ionization type particle detectors.

4. The apparatus of claim 1, wherein if the comparator determines that the difference between the first particulate concentration and the second particulate concentration exceeds a predetermined threshold, an alert signal is raised by the comparator.

5. The apparatus of claim 4, wherein the alert signal causes the electronic device to shut down.

6. The apparatus of claim 4, wherein the alert signal causes the electronic device to issue a warning to the user of the device.

7. The apparatus of claim 1, wherein if the comparator determines that the difference between the first particulate concentration and the second particulate concentration exceeds a predetermined threshold for a predetermined period of time, an alert signal is raised by the comparator.

8. The apparatus of claim 7, wherein the alert signal causes the electronic device to shut down.

9. The apparatus of claim 7, wherein the alert signal causes the electronic device to issue a warning to the user of the device.

10. A method of detecting a potential fire within an electronic device, the method including the steps of:
    detecting a first particulate concentration of all air passing into the electronic device at a first particulate sensor;
    detecting a second particulate concentration of all air passing out of the electronic device at a second particulate sensor; and comparing the first particulate concentration against the second particulate concentration, in order to detect an incipient fire condition within the device.

11. The method of claim 10, wherein the method further includes the step of:

issuing a warning to a user of the electronic device if the second particulate concentration exceeds the first particulate concentration by a predetermined margin.

12. The method of claim 10, wherein the method further includes the step of:

issuing a warning to a user of the electronic device if the second particulate concentration exceeds the first particulate concentration by a predetermined margin for a predetermined time interval.

13. The method of claim 10, wherein the method further includes the step of:

shutting down the electronic device if the second particulate concentration exceeds the first particulate concentration at a given time by a predetermined margin.

14. The method of claim 10, wherein the method further includes the step of:

shutting down the electronic device if the second particulate concentration exceeds the first particulate concentration by a predetermined margin for a predetermined time interval.

15. A program product, the program product comprising: signal bearing media; and a fire detection routine stored on said signal bearing media, said fire detection routine being configured to perform the following steps:

detecting a first particulate concentration of all air passing into the electronic device at a first particulate sensor;

detecting a second particulate concentration of all air passing out of the electronic device at a second particulate sensor; and comparing a first particulate concentration against a second particulate concentration, in order to detect an incipient fire condition within the electronic device.

16. The program product of claim 15, wherein the fire detection routine further performs the step of:

issuing a warning to a user of the electronic device if the second particulate concentration exceeds the first particulate concentration at a given time by a predetermined margin.

17. The program product of claim 15, wherein the fire detection routine further performs the step of:

issuing a warning to a user of the electronic device if the second particulate concentration exceeds the first particulate concentration by a predetermined margin for a predetermined time interval.

18. The program product of claim 15, wherein the fire detection routine further performs the step of:

shutting down the electronic device if the second particulate concentration exceeds the first particulate concentration at a given time by a predetermined margin.

19. The program product of claim 15, wherein the fire detection routine further performs the step of:

shutting down the electronic device if the second particulate concentration exceeds the first particulate concentration by a predetermined margin for a predetermined time interval.

* * * * *